United States Patent
Damasco et al.

(10) Patent No.: US 6,767,346 B2
(45) Date of Patent: Jul. 27, 2004

(54) CRYOSURGICAL PROBE WITH BELLOWS SHAFT

(75) Inventors: Sanford D. Damasco, Irvine, CA (US); Dennis M. Bui, Orange, CA (US); Xiaoyu Yu, San Diego, CA (US)

(73) Assignee: Endocare, Inc., Irvine, CA (US)

( * ) Notice: Subject to any disclaimer, the term of this patent is extended or adjusted under 35 U.S.C. 154(b) by 0 days.

(21) Appl. No.: 10/057,033

(22) Filed: Jan. 23, 2002

(65) Prior Publication Data

US 2003/0055416 A1 Mar. 20, 2003

Related U.S. Application Data

(63) Continuation-in-part of application No. 09/957,337, filed on Sep. 20, 2001.

(51) Int. Cl.[7] .............................................. A61B 17/36
(52) U.S. Cl. ............................ 606/21; 606/20; 606/22; 607/105; 607/113
(58) Field of Search ........................ 606/20–26; 607/96, 607/105, 113

(56) References Cited

U.S. PATENT DOCUMENTS

| | | | |
|---|---|---|---|
| 3,800,552 A | 4/1974 | Sollami | 62/293 |
| 3,913,581 A | 10/1975 | Ritson | 128/303.1 |
| 4,202,336 A | 5/1980 | Van Gerven | 128/303.1 |
| 5,108,390 A | 4/1992 | Potocky | 606/21 |
| 5,388,415 A | 2/1995 | Glinks | 62/51.2 |
| 5,452,582 A | 9/1995 | Longsworth | 62/51.2 |
| 5,522,870 A | 6/1996 | Ben Zion | 607/104 |
| 5,733,280 A * | 3/1998 | Avitall | 606/23 |
| 5,800,487 A | 9/1998 | Mikus | 607/105 |
| 5,899,899 A | 5/1999 | Arless | 606/22 |
| 5,957,963 A | 9/1999 | Dobak | 607/104 |
| 5,992,158 A | 11/1999 | Goddard | 62/51.2 |
| 6,074,412 A | 6/2000 | Mikus | 607/105 |
| 6,106,518 A | 8/2000 | Wittenberger | 606/23 |
| 6,110,192 A * | 8/2000 | Ravenscroft et al. | 606/194 |
| 6,161,543 A | 12/2000 | Cox | 128/898 |
| 6,224,624 B1 | 5/2001 | Lasheras | 607/105 |
| 6,235,019 B1 | 5/2001 | Lehmann | 606/22 |
| 6,238,428 B1 | 5/2001 | Werneth | 607/105 |
| 6,241,722 B1 | 6/2001 | Dobak | 606/23 |
| 6,355,029 B1 * | 3/2002 | Joye et al. | 606/21 |

OTHER PUBLICATIONS

Walker & Gingham, Low Capacity Cryogenic Refrigeration, pp. 67 ET SEQ (1994).

* cited by examiner

Primary Examiner—Rosiland K. Rollins
(74) Attorney, Agent, or Firm—Lawrence N. Ginsberg

(57) ABSTRACT

The malleable cryosurgical probe includes a cryostat assembly and a cryoprobe assembly. The cryostat assembly includes an elongated shaft assembly having a bellows portion thereof and a closed distal end. The shaft assembly includes at least one freezing portion comprising the bellows portion, at least one thermally insulated portion and a thermally insulating element positioned about the thermally insulated portion. A cryostat is operably associated with the elongated shaft assembly. It includes a cryostat inlet for receiving gas entering the cryostat, a cryostat outlet and a heat exchanger positioned between the cryostat outlet and the cryostat inlet. The heat exchanger receives gas from the cryostat inlet and provides heat transfer between gas flowing within the cryostat and fluid exterior thereto. At least one Joule-Thomson nozzle is in fluid communication with the cryostat outlet. The at least one Joule-Thomson nozzle expands gas expelled therefrom. The expanded cold fluid communicates with the freezing portion to provide cooling thereof. The cryoprobe assembly includes a handle assembly for supporting the cryostat assembly and a fluid supply line assembly connectable to a fluid source at one end and to the cryostat inlet at a second end. The heat exchanger is positioned at a location longitudinally spaced from the freezing portion(s).

13 Claims, 5 Drawing Sheets

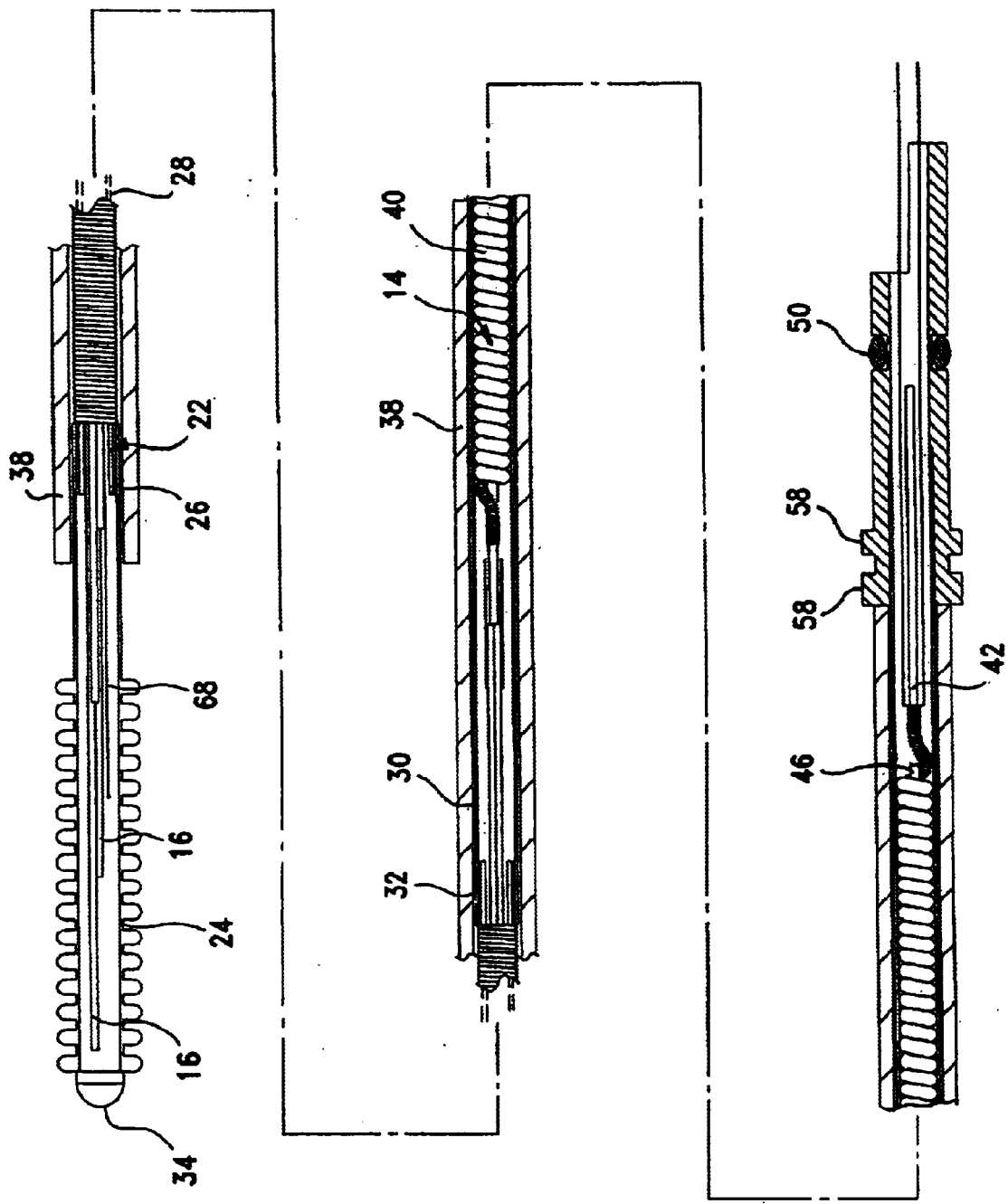

CRYOSURGICAL PROBE WITH BELLOWS SHAFT

CROSS REFERENCE TO RELATED APPLICATIONS

This application is a continuation-in-part of U.S. Ser. No. 09/957,337 filed Sep. 20, 2001.

BACKGROUND OF THE INVENTION

1. Field of the Invention

This invention relates to cryosurgical probes and more particularly to a cryosurgical probe that includes an improved malleable shaft for use with applications in which a desired angle of entry and contact with the patient's organ is required.

2. Description of the Related Art

Cryosurgical probes are used to treat a variety of diseases. The cryosurgical probes quickly freeze diseased body tissue, causing the tissue to die after which it will be absorbed by the body, expelled by the body, sloughed off or replaced by scar tissue. Cryothermal treatment is currently used to treat prostate cancer and benign prostate disease, breast tumors including breast cancer, liver tumors including cancer, glaucoma and other eye diseases. Cryosurgery may also be used for the treatment of a number of other diseases and conditions including the treatment of cardiac arrhythmias, such as atrial fibrillation.

A variety of cryosurgical instruments variously referred to as cryoprobes, cryosurgical probes, cryosurgical ablation devices, and cryostats and cryocoolers, have been available for cryosurgery. These devices typically use the principle of Joule-Thomson expansion to generate cooling. They take advantage of the fact that most fluids, when rapidly expanded, become extremely cold. In these devices, a high pressure gas such as argon or nitrogen is expanded through a nozzle inside a small cylindrical shaft or sheath typically made of steel, and the Joule-Thomson expansion cools the steel sheath to a cold temperature very rapidly.

An exemplary device is illustrated in Sollami, Cryogenic Surgical Instrument, U.S. Pat. No. 3,800,552 (Apr. 2, 1974). Sollami shows a basic Joule-Thomson probe with a sheath made of metal, a fin-tube helical gas supply line leading into a Joule Thomson nozzle which directs expanding gas into the probe. Expanded gas is exhausted over the fin-tube helical gas supply line, and pre-cools incoming high pressure gas. For this reason, the coiled supply line is referred to as a heat exchanger, and is beneficial because, by pre-cooling incoming gas, it allows the probe to obtain lower temperatures.

Ben-Zion, Fast Changing Heating and Cooling Device and Method, U.S. Pat. No. 5,522,870 (Jun. 4, 1996) applies the general concepts of Joule-Thomson devices to a device that is used first to freeze tissue and then to thaw the tissue with a heating cycle. Nitrogen is supplied to a Joule-Thomson nozzle for the cooling cycle, and helium is supplied to the same Joule-Thomson nozzle for the warming cycle. Preheating of the helium is presented as an essential part of the invention, necessary to provide warming to a sufficiently high temperature.

A Joule-Thomson cryostat for use as a gas tester is illustrated in Glinka, System for a Cooler and Gas Purity Tester, U.S. Pat. No. 5,388,415 (Feb. 14, 1995). Glinka also discloses use of the by-pass from the Joule-Thomson Nozzle to allow for cleaning the supply line, and also mentions that the high flow of gas in the by-pass mode will warm the probe. This is referred to as mass flow warming, because the warming effect is accomplished purely by conduction and convection of heat to the fluid mass flowing through the probe.

Various cryocoolers use mass flow warming, flushed backwards through the probe, to warm the probe after a cooling cycle. Lamb, Refrigerated Surgical Probe, U.S. Pat. No. 3,913,581 (Aug. 27, 1968) is one such probe, and includes a supply line for high pressure gas to a Joule-Thomson expansion nozzle and a second supply line for the same gas to be supplied without passing through a Joule-Thomson nozzle, thus warming the catheter with mass flow. Longsworth, Cryoprobe, U.S. Pat. No. 5,452,582 (Sep. 26, 1995) discloses a cryoprobe which uses the typical fin-tube helical coil heat exchanger in the high pressure gas supply line to the Joule-Thomson nozzle. The Longsworth cryoprobe has a second inlet in the probe for a warming fluid, and accomplishes warming with mass flow of gas supplied at about 100 psi. The heat exchanger, capillary tube and second inlet tube appear to be identical to the cryostats previously sold by Carleton Technologies, Inc. of Orchard Park, N.Y.

Each of the above mentioned cryosurgical probes builds upon prior art which clearly establishes the use of Joule-Thomson cryocoolers, heat exchangers, thermocouples, and other elements of cryocoolers. Walker, *Miniature Refrigerators for Cryogenic Sensor and Cold Electronics* (1989) (Chapter 2) and Walker & Gingham, Low *Capacity Cryogenic Refrigeration*, pp. 67 et seq. (1994) show the basic construction of Joule-Thomson cryocoolers including all of these elements. The Giaque-Hampson heat exchanger, characterized by coiled finned-tube, transverse flow recuperative heat exchanger is typical of cryocoolers. The open mandrel around which the finned tube coil is placed is also typical of cryocoolers.

U.S. Pat. Nos. 5,800,487 and 6,074,412, both entitled Cryoprobe, issued to Mikus et and assigned to the present assignee disclose cryoprobes using Joule-Thomson nozzles and finned tube helical coil heat exchangers.

Cryosurgical probes may be used, as mentioned above, to treat diseases of the prostate, liver, and breast, and they have gynecological applications as well. The cryosurgical probes form iceballs which freeze disease tissue. Each application has a preferred shape of iceball, which, if capable of production, would allow cryoablation of the diseases tissue without undue destruction of surrounding healthy tissue. For example, prostate cryoablation optimally destroys the lobes of the prostate, while leaving the surrounding neurovascular bundles, bladder neck sphincter and external sphincter undamaged. The prostate is wider at the base and narrow at the apex. A pear or fig shaped ice ball is best for this application. Breast tumors tend to be small and spherical, and spherical iceballs will be optimal to destroy the tumors without destroying surrounding breast tissue. Liver tumors may be larger and of a variety of shapes, including spherical, olive shaped, hot dog shaped or irregularly shaped, and may require more elongated iceballs, larger iceballs, and iceballs of various shapes.

During open chest surgery transmural cryo-lesions can be created on or in the heart to treat cardiac arrhythmia (including atrial fibrillation). A suitable cryoprobe would be useful for this application. Due to the nature of the procedure and anatomical locations that lesions must be placed, the cryoprobe must be sufficiently malleable by the surgeon to be placed on the heart surface but stiff enough such that pressure can be applied without flexing the shaft.

The prior art includes references to malleable and flexible cryoprobes. For example, U.S. Pat. No. 6,161,543, issued to Cox et al discloses the use of a malleable probe. The probe has a malleable shaft. A malleable metal rod is coextruded with a polymer to form the shaft. The rod permits the user to shape the shaft as necessary so that a tip can reach the tissue to be ablated.

U.S. Pat. No. 5,108,390, issued to Potocky et al discloses a highly flexible cryoprobe that can be passed through a blood vessel and into the heart without external guidance other than the blood vessel itself.

Several patents disclose the use of bellows-type assemblies for use with cryosurgical systems. For example, U.S. Pat. No. 6,241,722, issued to Dobak et al, discloses a cryogenic catheter with a bellows and which utilizes a longitudinally movable Joule-Thomson nozzle of expansion. The Dobak '722 device preferably uses closed media-flow pathways for efficient recycling of the media employed.

Dobak, in his U.S. Pat. No. 5,957,963, disclose the used of a flexible catheter inserted through the vascular system of a patient to place the distal tip of the catheter in an artery feeding a selected organ of the patient. The '963 patent discloses a heat transfer bellows for cooling the blood flowing through the artery.

U.S. Pat. No. 6,235,019, issued to J. W. Lehmann et al, discloses a cryosurgical catheter having a bellows. The cryogenic catheter has an elongate outer member and a plurality of inner members disposed with the elongate outer member. The inner members define at least one cryogenic path through the outer member. At least one of the inner members has at least one controllable opening formed thereon to selectively release cryogenic fluid. The inner members also include an overtube and an injection tube slideably disposed to one another.

U.S. Pat. No. 6,106,518, issued to Wittenberger et al, discloses a medical device that includes a flexible member having a variable geometry tip with a thermally-transmissive region. A smooth fluid path is provided through the flexible member to and from a variable geometry, thermally-transmissive region. The thermally-transmissive region may be a bellows-like structure.

U.S. Pat. No. 6,224,624, issued to Lasheras et al, discloses a bellows structure used for a selective organ heat transfer device having a flexible coaxial catheter capable of insertion into a selected feeding artery in the vascular system of a patient.

SUMMARY

In a broad aspect, the present invention is a malleable cryosurgical probe comprising a cryoassembly for providing a flow of cryogenic fluid and a malleable shaft secured to and in heat transfer relationship with the cryoassembly. The shaft has a bellows portion located thereon formed of a thermally conductive metal. The bellows portion has a plurality of convolutions, the convolutions having outer diameters in a range of 0.140–0.180 inches, and inner diameters in a range of 0.065–0.100 inches. The bellows portion has a minimum bend radius of about 0.195 inches, thus being bendable as desired by the operator.

In another broad aspect, the cryosurgical probe includes a cryostat assembly and a cryoprobe assembly. The cryostat assembly includes an elongated shaft assembly having a bellows portion thereof and a closed distal end. The shaft assembly includes at least one freezing portion comprising said bellows portion, at least one thermally insulated portion and a thermally insulating element positioned about the thermally insulated portion. A cryostat is operably associated with the elongated shaft assembly. It includes a cryostat inlet for receiving gas entering the cryostat, a cryostat outlet and a heat exchanger positioned between the cryostat outlet and the cryostat inlet. The heat exchanger receives gas from the cryostat inlet and provides heat transfer between gas flowing within the cryostat and fluid exterior thereto. At least one Joule-Thomson nozzle is in fluid communication with the cryostat outlet. The at least one Joule-Thomson nozzle expands gas expelled therefrom. The expanded cold fluid communicates with the freezing portion to provide cooling thereof. The cryoprobe assembly includes a handle assembly for supporting the cryostat assembly and a fluid supply line assembly connectable to a fluid source at one end and to the cryostat inlet at a second end. The heat exchanger is positioned at a location longitudinally spaced from the freezing portion(s).

Positioning of the heat exchanger in a position longitudinally spaced from the freezing portion(s) provides the capability of providing malleable segments. The heat exchanger can be made relatively large and powerful providing enhanced operation while concomitantly providing for a freezing portion and/or thermally insulated portion of the elongated shaft assembly that has a small diameter. The bellows portion formed of material that permits reshaping and bending of the elongated shaft assembly as a unit to reposition the ablating surface for greater ablation precision. Moreover, enhancements are disclosed for assuring that there can be bending and reshaping without kinking or collapsing. Such properties are especially imperative for such devices employed in the formation of transmural lesions in anatomical locations that are particularly difficult to access. The malleable segment is sufficiently malleable to be fashioned to the desired shape while rigid enough to retain the shape during clinical use.

Other objects, advantages, and novel features will become apparent from the following detailed description of the invention when considered in conjunction with the accompanying drawings.

BRIEF DESCRIPTION OF THE DRAWINGS

FIG. 5 is an enlarged view of the cryostat assembly of the cryosurgical probe of FIG. 1 with the handle removed for the purposes of clarity.

The same parts or elements throughout the drawings are designated by the same reference characters.

DETAILED DESCRIPTION OF THE INVENTION

Figure 1:
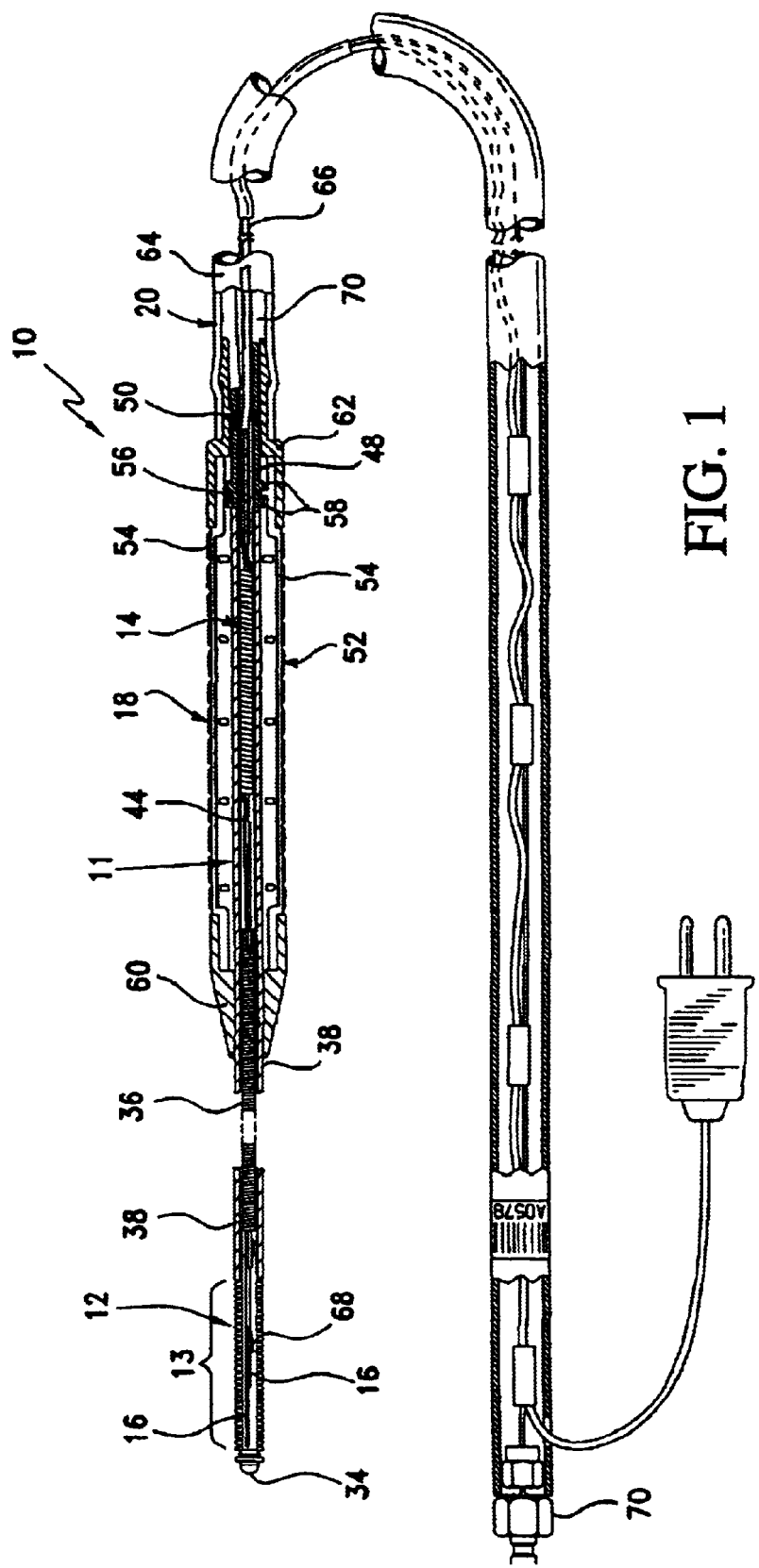
FIG. 1 is a crossectional view of a preferred embodiment of the cryosurgical probe of the present invention.

Referring to the drawings and the characters of reference marked thereon FIG. 1 illustrates a preferred embodiment of the present invention, designated generally as 10. The malleable cryosurgical probe 10 includes a cryoassembly, designated generally as 11, for providing a flow of cryogenic fluid and a malleable shaft assembly, designated generally as 12. The malleable shaft assembly 12 is in heat transfer relationship with the cryoassembly 11. The shaft includes a bellows portion 13 formed of thermally conductive metal. The cryoassembly 11 will be discussed in detail below.

Figure 2:
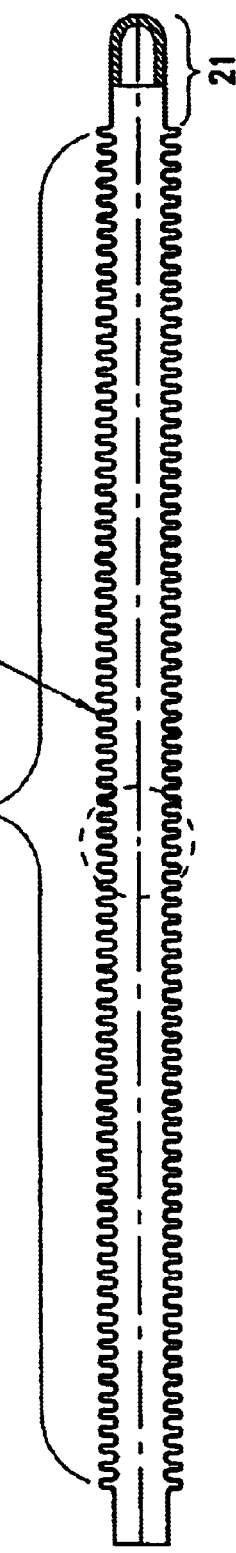
FIG. 2 is a crossectional view of the bellows shaft of the cryosurgical probe of the present invention.
Figure 3:
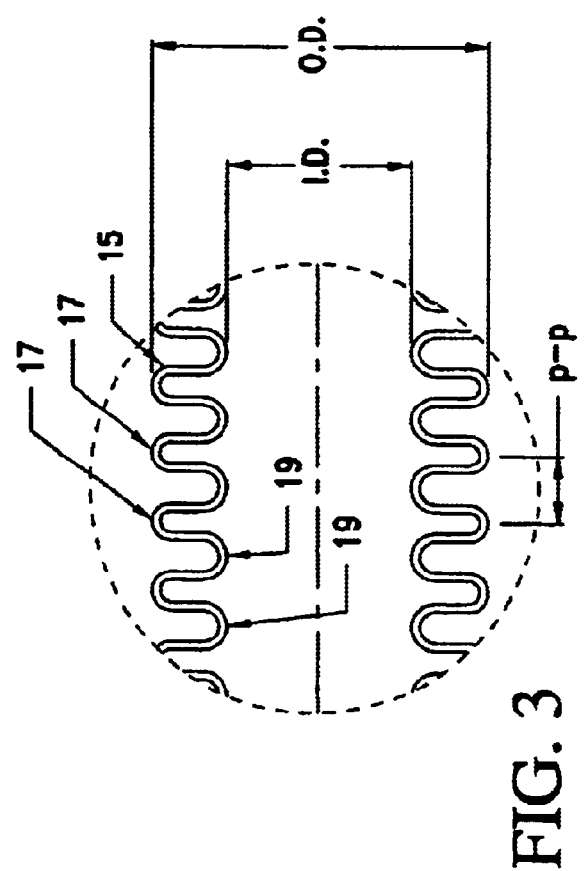
FIG. 3 is an enlarged crossectional view of a portion of the bellows shaft of the present invention to show the convolutions.

Referring now to FIGS. 2 and 3 the shaft assembly 12 is illustrated. As best seen in FIG. 3 the bellows portion 13 of the shaft assembly 12 includes a plurality of convolutions 15. These convolutions 15 have outer diameters (OD's) preferably in a range of 0.140–0.180 inches and inner diameters (ID's) preferably in a range of 0.065–0.100 inches. The bellows portion 13 has a minimum bend radius of about 0.195 so that the bellows portion is bendable as desired by the operator. It is preferably formed by hydroforming techniques.

Each convolution 15 comprises a peak section 17 and a valley section 19. The peck sections each have peaks such that the convolutions, containing these alternating peak sections 17 and valley sections 19, are preferably spaced in a range of 0.020–0.100 inches, peak-to-peak (P—P). Preferably, the convolutions 15 are spaced in a range of 0.030 inches, peak-to-peak. The wall thickness is preferably in a range of 0.0015 to 0.0122 inches.

Figure 4:
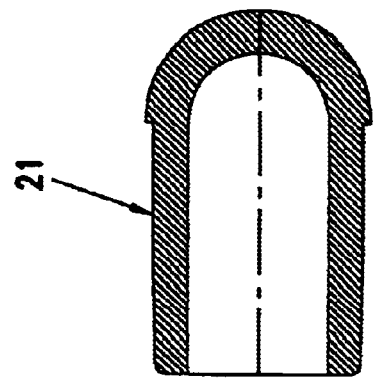
FIG. 4 is an enlarged crossectional view of the tip of the bellows shaft.

As can be seen most clearly in FIG. 4 a tip portion 21 is located at the distal end of the shaft assembly wherein the distance between the tip of the tip portion and the bellows portion is preferably no more than 1½ of the OD's of the convolutions 15.

Referring again to FIG. 1 and also now to FIG. 5 it can be seen that the cryosurgical probe 10 may be deemed to include a cryostat assembly and a cryoprobe assembly. The cryostat assembly includes the elongated shaft assembly 12, a cryostat designated generally as 14, and Joule-Thomson nozzles 16. The cryoprobe assembly includes a handle assembly, designated generally as 18 and a fluid supply line assembly 20.

The elongated shaft assembly 12 includes a main body portion 22 and a distal portion 24 welded thereto with a spacer 26. The main body portion 22 includes a thermally protected segment 28 and an adapter segment 30, these two segments being welded together with a spacer 32. The thermally protected segment 28 is positioned between the adapter segment 30 and the distal portion 24. The distal portion 24 comprises the malleable bellows portion 13. Both the main body portion 22 and the distal portion 24 are generally tubular elements. They may be formed of, for example, annealed metals such as annealed stainless steel, annealed nickel or annealed copper. The elongated shaft assembly may have a wide range of lengths depending on the desired purpose, i.e. it might be one to perhaps twenty inches long.

A shaft enhancement element such as a spring coil member 36 may be positioned about the tube of the thermally protected segment 28. The spring coil member 36 enhances the capability of the thermally protected segment 28 of bending and reshaping without kinking or collapsing.

The elongated shaft assembly includes a thermally insulating element 38 positioned over the main body portion 22 to define a thermally insulated portion. The portion of the distal portion 24 that remains uncovered and includes the bellows portion 13 defines a freezing portion. The freezing portion is preferably made of a thermally conductive material, such as stainless steel, as noted above. The elongated shaft assembly 12 has been shown with three different parts, i.e. segment 28, adapter segment 30 and distal portion 24. This is to accommodate various desired sizes of distal portions 24. However, use of these three parts has been shown by way of illustration and not limitation. For example, a one-piece shaft can be utilized. The thermally insulated portion typically has an outer diameter in a range of between about 0.04 inches and about 0.50 inches, preferably in a range of about 0.10 inches and about 0.15 inches.

The cryostat 14 comprises a coiled heat exchanger 40. A cryostat inlet 42 receives gas entering the cryostat while a cryostat outlet 44 provides the gas to the Joule-Thomson nozzles 16. The coiled heat exchanger 40 is coiled around a mandrel 46. In between each winding of the heat exchanger, gaps are formed between the coil and the main body portion 22, and gaps are formed between the coil and the mandrel 46. This construction is known as a Giaque-Hampson heat exchanger. The heat exchanger, which is an integral part of the high pressure gas pathway, is made with finned tubing, with numerous fins throughout its length.

The handle assembly 18 includes an anchor 48 securely connected to the cryostat assembly by welding or other conventional means. An o-ring 50 prevents fluid from escaping through the handle assembly 18. A handle, designated generally as 52, includes two elongated opposing handle body elements 54 with radially inward extensions 56 for engaging the space between radially outward extensions 58 of the anchor 48. A handle nozzle 60 fits over and secures the handle body elements 54 together at first ends thereof via a friction fit. A handle barb 62 secures the handle body elements 54 together at second ends thereof.

The fluid supply line assembly 20 includes a housing 64 that supports a fluid supply line 66. A temperature measurement device, i.e. a thermocouple 68, is positioned within the elongated shaft assembly, extends through the fluid supply line assembly 20 and is connectable to a data acquisition system. The thermocouple 68 is used to measure and monitor the temperature inside the cryosurgical probe.

Fluid flow through the cryosurgical probe is as follows. High pressure fluid, preferably gaseous argon, and generally at a pressure in a range of about 2000 psi to about 4500 psi, typically about 3000 psi, is supplied to the assembly through high pressure fitting 70, flows through gas supply line 66, through cryostat inlet 42, into heat exchanger 40, through cryostat outlet 44 and Joule-Thomson nozzles 16. (In a preferred embodiment, for the treatment of arrythmia, five Joule-Thomson nozzles are utilized.) The high pressure gas expands within the expansion chamber and cools to cryogenic temperatures. The temperature at the Joule-Thomson nozzles 16 is generally at a first temperature of about 20° C. and expands to a temperature of about −150° C. Condensation of the gas is preferably avoided but can be tolerated. After expanding, the gas is at lower pressure and exhausts over the exhaust gas pathway that includes flow over outside of the coils of the heat exchanger 40. Because it is now cold, it cools the gas flowing inside the coils. This makes cooling more efficient and achieves colder temperatures. After passing through the heat exchanger, the exhaust gas flows through the remainder of the exhaust gas pathway, as indicated by numeral designation 70. The exhaust gas is eventually vented to the atmosphere.

Prior art warming methods such as exhaust blocking, reverse flow heat transfer, and electrical heating can be employed. The preferred method of warming is to supply high pressure helium gas through the supply line, heat exchanger and Joule-Thomson nozzle. Helium gas heats up when expanded through the gas outlet. Thus, the supply of gas to the probe can be switched from high pressure nitrogen or argon to high pressure helium to effect rapid re-warming of the cryosurgical probe.

Figure 6:
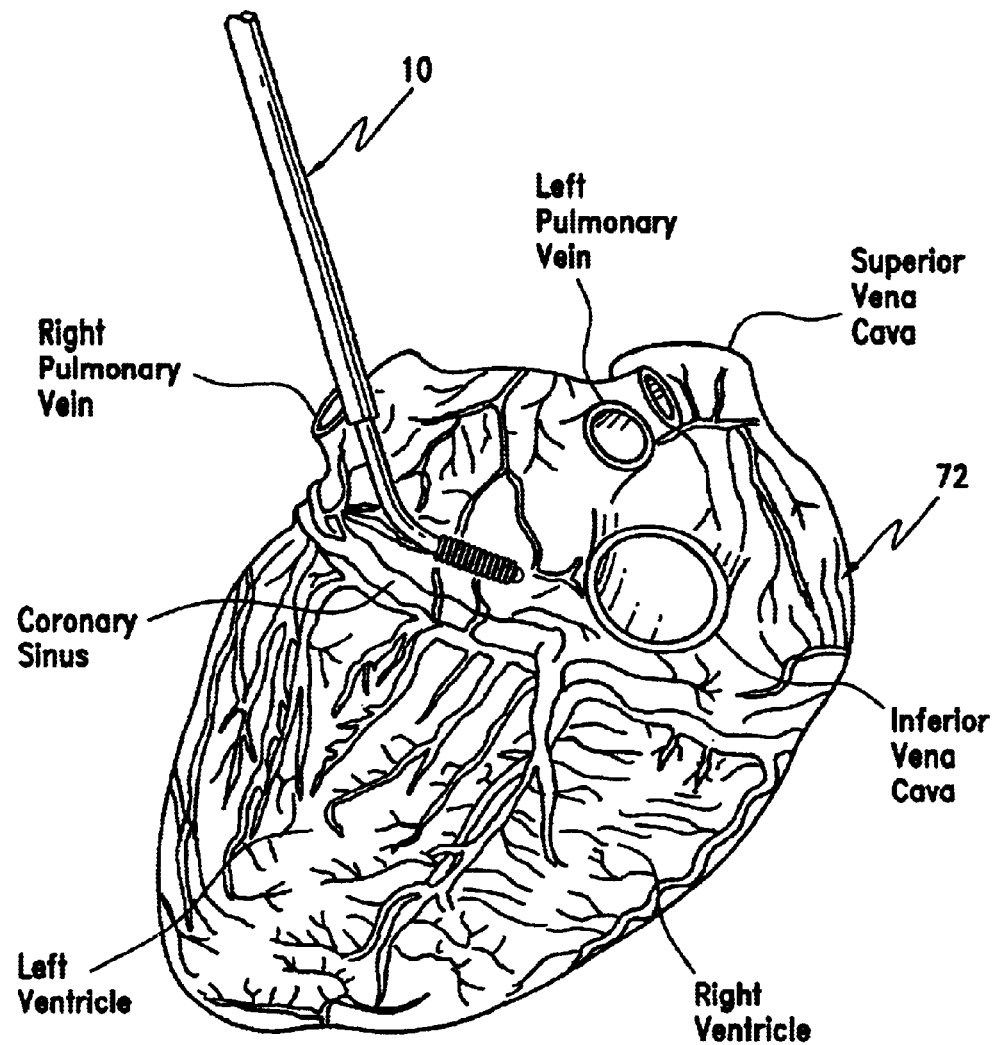
FIG. 6 is a schematic view of the heart with the cryosurgical probe of the present invention shown positioned thereagainst for the treatment of arrhythmias.

Referring now to FIG. 6, the utilization of the present cryosurgical probe 10, positioned against the heart 72, for treating arrhythmias, is illustrated. This creates transmural lesions that have the effect of channeling, limiting or blocking electrical transmissions. Its malleable characteristics allow the cryosurgical probe 10 to create elongated homogenous lesions (either curved or straight) at desired locations that are often difficult to access with a straight surgical implement.

For such treatment of arrhythmia the bellows portion 13 should may be in a range of about 1.5–4.0 inches long, preferably in a range of about 2.6–3.2 inches long. The preferred length is about 2.7 inches.

Use of the longitudinally spaced Joule-Thomson nozzles 16 provides the ability to create elongated iceballs as desired along the length of the bellows portion 13. Although the embodiment illustrated shows four Joule-Thomson nozzles 16, more or less can be provided depending on the particular requirements. Use of this plurality of Joule-Thomson nozzles 16 is made possible, in part, because of the spacing of the heat exchanger from them.

Figure 7:
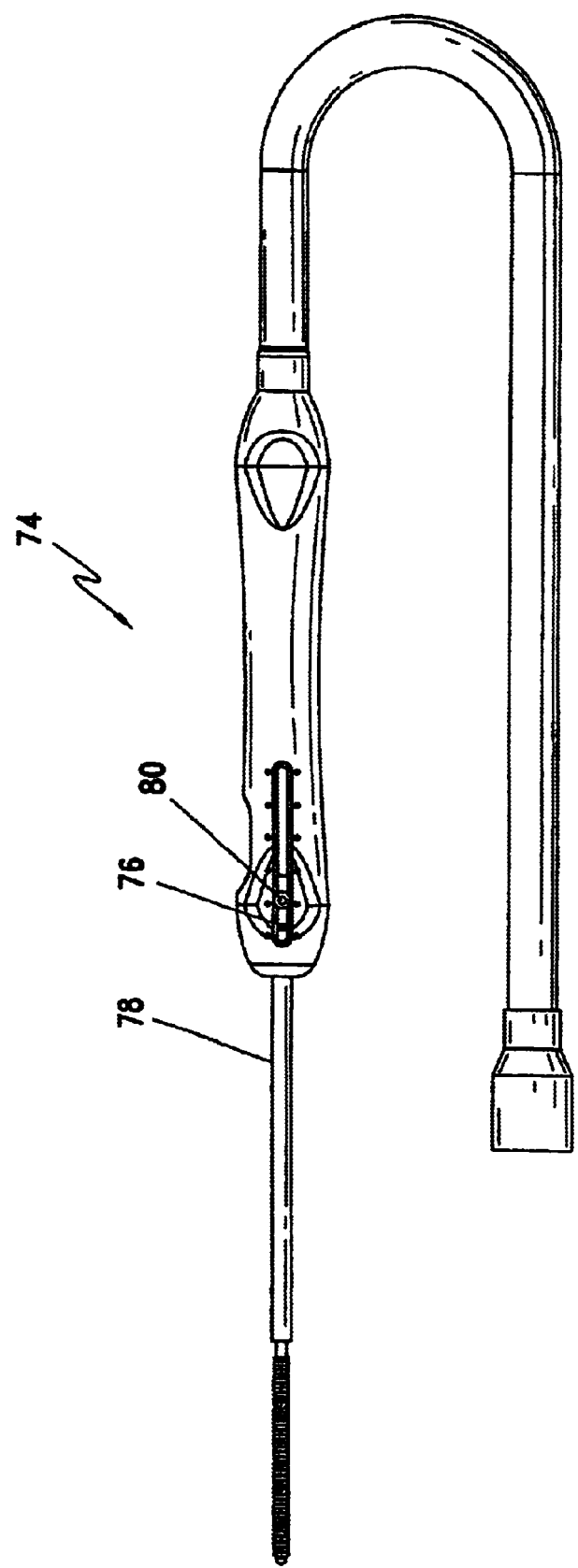
FIG. 7 is a schematic illustration of an embodiment of the cryosurgical probe having a movable, thermally insulated main portion.

Referring now to FIG. 7 another embodiment of the cryosurgical probe is illustrated, designated generally as 74. In this embodiment a sliding assembly including a sliding element 76 attached to a thermal insulating element 78 is utilized to cover the bellows portion as desired to control ice formation. The sliding element includes a button 80 to provide ease in such adjustments.

Obviously, many modifications and variations of the present invention are possible in light of the above teachings. It is, therefore, to be understood that within the scope of the appended claims, the invention may be practiced otherwise than as specifically described.

What is claimed and desired to be secured by Letters Patent of the United States is:

1. A malleable cryosurgical probe, comprising:
   a cryoassembly for providing a flow of cryogenic fluid, said cryoassembly comprising a plurality of longitudinally spaced Joule-Thomson nozzles; and,
   a malleable shaft secured to and in heat transfer relationship with said cryoassembly, said shaft having a hydroformed bellows portion located thereon formed of a thermally conductive metal, said bellows portion having a plurality of convolutions, said convolutions having outer diameters in a range of 0.140–0.180 inches and inner diameters in a range of 0.065–0.100 inches, said bellows portion having a minimum bend radius of about 0.195 inches, said convolutions each comprise peak sections and valley sections, said peak sections each having peaks, said convolutions being spaced in a range of 0.020–0.100 inches, peak-to-peak, wherein each convolution has a wall thickness in a range of 0.0015 to 0.0122 inches and wherein said bellows portion is bendable and will hold form as desired by the operator.

2. The malleable cryosurgical probe of claim 1, wherein said convolutions each comprise alternating peak sections and valley sections, said peak sections each having peaks, said convolutions being spaced by a distance of approximately 0.030 inches, peak-to-peak.

3. The malleable cryosurgical probe of claim 1, wherein said convolutions each comprise alternating peak sections and valley sections, each valley section defining a valley radius and each peak section defining a peak radius, the summation of said valley radius and said peak radius being one-half the peak-to-peak distance between convolutions.

4. The malleable cryosurgical probe of claim 1, wherein said shaft comprises a tip portion at a distal end thereof wherein the distance between a tip of said tip portion and said bellows portion is no more than 1½ times the outer diameters of said convolutions.

5. The malleable cryosurgical probe of claim 1, wherein said cryoassembly comprises a sliding assembly including a sliding element attached to a thermal insulating element for selectively effecting the location of the freezing zone.

6. The malleable cryosurgical probe of claim 1 wherein said bellows portion has a length in a range of 1.4 inches to about 4.0 inches.

7. The malleable cryosurgical probe of claim 1 wherein said cryogenic fluid is introduced to said Joule-Thomson nozzles at a rate of between about 2000 psi to about 4500 psi.

8. A malleable cryosurgical probe, comprising:
   a) a cryostat assembly, comprising:
      i) an elongated shaft assembly having at least one malleable hydroformed bellows portion thereof and a closed distal end, said shaft assembly, including:
         at least one freezing portion comprising said at least one bellows portion;
         at least one thermally insulated portion: and,
         a thermally insulating element positioned about said thermally insulated portion;
      ii) a cryostat operably associated with said elongated shaft assembly, comprising:
         a cryostat inlet for receiving gas entering said cryostat;
         a cryostat outlet; and,
         a heat exchanger positioned between said cryostat outlet and said cryostat inlet, said heat exchanger for receiving gas from said cryostat inlet and providing heat transfer between gas flowing within said cryostat and fluid exterior thereto; and,
      iii) a plurality of longitudinally spaced Joule-Thomson nozzles in fluid communication with said cryostat outlet, said plurality of Joule-Thomson nozzles for expanding gas expelled therefrom, the expanded cold fluid communicating with said at least one freezing portion to provide cooling thereof; and,
   b) a cryoprobe assembly, comprising:
      a handle assembly for supporting said cryostat assembly; and,
      a fluid supply line assembly connectable to a fluid source at one end and to said cryostat inlet at a second end,
   wherein said heat exchanger is positioned at a location longitudinally spaced from said at least one freezing portion
   wherein said bellows portion is formed of a thermally conductive metal, said bellows portion having a plurality of convolutions, said convolutions having outer diameters in a range of 0.140–0.180 inches and inner diameters in a range of 0.065–0.100 inches, said bellows portion having a minimum bend radius of about 0.195 inches, said convolutions each comprise peak sections and valley sections, said peak sections each having peaks, said convolutions being spaced in a range of 0.020–0.100 inches, peak-to-peak, wherein each convolution has a wall thickness in a range of 0.0015 to 0.0122 inches and wherein said bellows portion is bendable and will hold form as desired by the operator.

9. The malleable cryosurgical probe of claim 8, wherein said convolutions each comprise alternating peak sections and valley sections, said peak sections each having peaks, said convolutions being spaced by a distance of approximately 0.030 inches, peak-to-peak.

10. The malleable cryosurgical probe of claim 8, wherein said convolutions each comprise alternating peak sections and valley sections, each valley section defining a valley radius and each peak section defining a peak radius, the summation of said valley radius and said peak radius being one-half the peak-to-peak distance between convolutions.

11. The malleable cryosurgical probe of claim 8, wherein said cryostat assembly comprises a sliding assembly including a sliding element attached to said thermally insulating element for selectively effecting the location of the freezing zone.

12. The malleable cryosurgical probe of claim 8, wherein said handle assembly defines a volume formed therein, said heat exchanger being positioned within said volume.

13. The malleable cryosurgical probe of claim 8, wherein said thermally insulating element is adjustably positionable to control the location, size and shape of said freezing portion.

* * * * *